United States Patent [19]

Lather et al.

[11] 4,106,326
[45] Aug. 15, 1978

[54] INITIALIZATION AND PREPARATION OF ON-PRODUCTION-LINE ULTRASONIC TEST EQUIPMENT

[75] Inventors: Dieter Lather, Rheurdt; Karl Ries, Mülheim, both of Fed. Rep. of Germany

[73] Assignee: Mannesmann Aktiengesellschaft, Dusseldorf, Fed. Rep. of Germany

[21] Appl. No.: 782,451

[22] Filed: Mar. 29, 1977

[30] Foreign Application Priority Data

Mar. 29, 1976 [DE] Fed. Rep. of Germany ....... 2613799

[51] Int. Cl.$^2$ ............................................. G01N 29/04
[52] U.S. Cl. ..................................... 73/1 DV; 73/614
[58] Field of Search ............... 73/1 DV, 67.5 R, 67.7, 73/67.8 R, 67.8 S, 67.9, 610, 614, 615, 616

[56] References Cited

U.S. PATENT DOCUMENTS

| | | | |
|---|---|---|---|
| 3,090,224 | 5/1963 | Rankin | 73/67.9 |
| 3,608,352 | 9/1971 | Walton et al. | 73/67.7 |
| 3,608,361 | 9/1971 | Krautkramer et al. | 73/67.7 |
| 3,688,565 | 9/1972 | Brech | 73/67.9 |
| 3,791,199 | 2/1974 | Toth et al. | 73/67.9 |

*Primary Examiner*—Stephen A. Kreitman
*Attorney, Agent, or Firm*—Ralf H. Siegemund

[57] ABSTRACT

The initialization and preparation procedure described involves particularly ultrasonic test equipment for ultrasonic inspection of welding seams of pipes while passing through a production line. A dummy is used off line to determine suitable distances and orientation of test heads and to acquire relevant transit time and amplitude data. A standard is then used to obtain additional reference data to be related to the dummy test data. After the test heads are installed in the production line test stand, tests are repeated with the standard to obtain now the needed test reference data in conjunction with the previously related data. This way, looking windows for flaw echos as well as sensitivity data for the subsequent tests are accurately and reproducibly predetermined.

4 Claims, 6 Drawing Figures

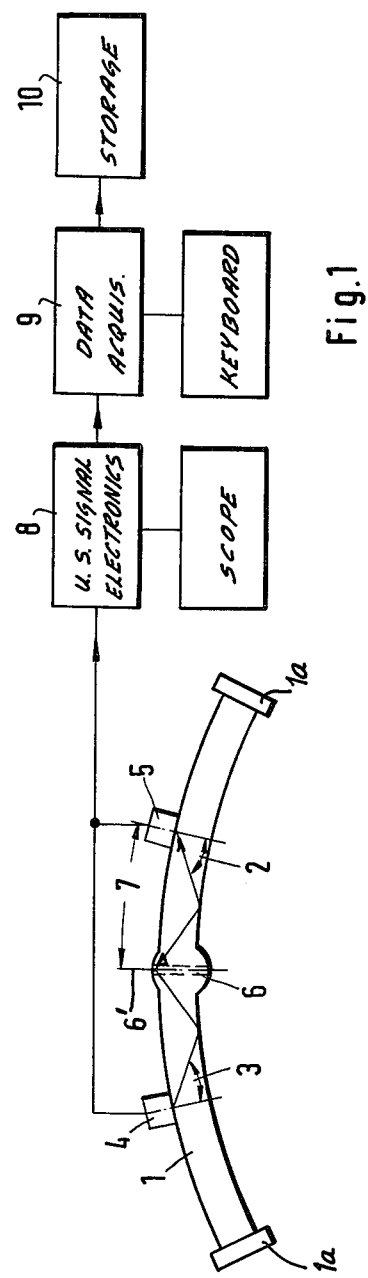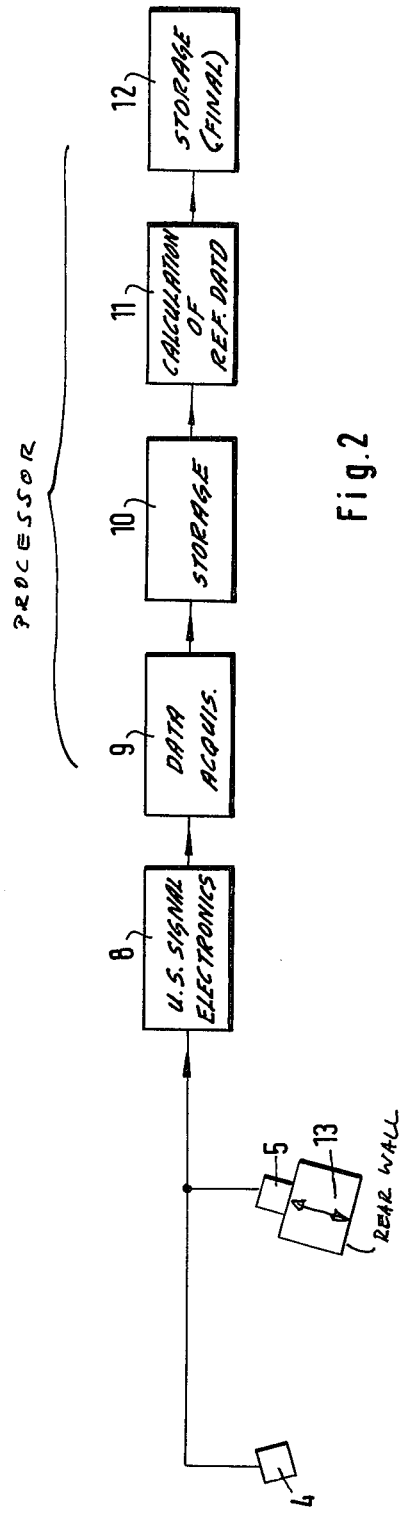

INITIALIZATION AND PREPARATION OF ON-PRODUCTION-LINE ULTRASONIC TEST EQUIPMENT

BACKGROUND OF THE INVENTION

The present invention relates to initialization and preparation of ultrasonic test stands and equipment for subsequent testing of objects, such as large pipes as to defects, e.g., in welding seams.

Ultrasonic test stands for testing, e.g., the longitudinal or helical welding seam of pipes, require a more or less extensive preparatory procedure before testing proper can begin. First of all, one uses dummies representing the objects expected to be tested. These dummies must have the dimensions as well as ultrasonic transmission and absorption characteristics equal to or in representation of the test objects. The dummy is provided with bores, grooves or the like of well defined dimensions, which are expected to produce particular interference with an ultrasonic probing beam. Since the dummy is actually used for simulation, the type of its grooves, notches, etc., will depend on the type of test, test specifications, etc.

This dummy is used to adjust, position and orient the test heads and their holders generally, whereby particularly parameters such as the distance from the expected welding seam, the sensitivity of test circuitry, the angles of incidence, skip distance, etc., are appropriately adjusted.

The test sensitivity is a particularly critical parameter due to its intimate relation to the response threshold of the test equipment. Proper selection of the grooves, etc., in the dummy for purposes of simulation is, therefore, quite important for the preparation of the equipment.

The known preparation and initialization procedures have posed a variety of problems, and have not yielded satisfactory results. For example, it is difficult to simulate the tolerances in accordance with prescribed test procedures and specifications. This is particularly the case when dummies are prepared to represent pipes or strips.

Another problem is the production of suitable dummies. They are quite expensive to make, e.g., in the case of pipes. It was found that it is actually necessary to use a portion of such a pipe itself. Defects can be simulated only after the dimensions of the section have been determined. Since ultrasonic testing of tubes or pipes in the production line requires incorporation of the equipment in that line, e.g., behind the welding station, it will be necessary to start the line and to take a sample from the first pipe passing through. Next, the dummy is made therefrom and only then will the ultrasonic test equipment be adjusted. Thus, an inherent extensive delay is incurred between this halted beginning and the resumption of production.

Another problem encountered is the weight of the dummy, again particularly when representing a large pipe. Handling of that dummy for purposes of equipment adjusted is greatly impeded by that weight. One needs cranes, vehicles, etc., just for moving the dummy into the desired positions. The sizes of the dummies pose the additional problem of storage.

Another problem relates to the aspect of reproducibility. Previous methods and procedures suffered because of inadequacy on that account. For example, reproducible positioning of the test equipment requires, for example, establishing of accurate and definable angles of incidence for the ultrasonic test beam into the object. Also, specific distances must be established.

It was found that "defects" in dummies do not permit adequate adjustment of that angle, agle, and equipment spacing can also be approximated only. The reason is that the equipment is positioned by an operator and is thus subjective. Also, similar test defects will exhibit different reflectivity in different dummies and objects because of differences in overall geometry as well as because of tolerances in generating the test defects.

DESCRIPTION OF THE INVENTION

It is an object of the present invention to provide for a new and improved initialization and preparation procedure for ultrasonic test equipment operated in a production line.

In accordance with the present invention, the following preparation and initialization steps are taken. A dummy is prepared, representing the zone participating in the ultrasonic inspection, and the test heads are disposed thereon in representation of the position and orientation, they are expected to have and to assume in the test stand. Following the appropriate adjustments, tests are run to obtain reference data being comprised basically of relative transit times and amplitudes. These data are acquired and stored, e.g., digitally in conjunction with relevant data for the test heads, the adjusted angles, etc. These tests are run outside of the production line and off the test stands thereof, e.g., in a separate test room, lab, etc. Still prior to the installation of the heads in the production line test equipment as well as subsequently thereto, a standard is interfaced with the heads and reference tests are run. On the basis of the reference data obtained in test runs before the installation and taken in relation to the dummy test data, the reference data obtained under utilization of the standard after installation, are used to derive therefrom the necessary test reference data for the on-production-line tests, including particularly the timing for gating operations for purposes of generating looking windows for echo signals, and further including the adjustment of the sensitivity.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a schematic view and block diagram of equipment being adjusted in relation to a dummy of, and representing a test object (pipe) in accordance with a first phase of the initialization and preparation procedure in accordance with the preferred embodiment;

FIG. 2 is a schematic view and block diagram of the same and additional equipment for operations pursuant to a second phase using a calibration dummy;

Figure 3A:
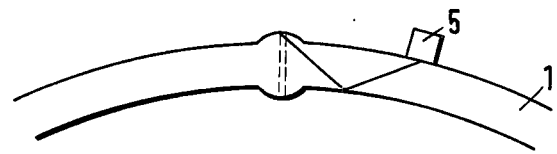
FIG. 3a is a sketch for facilitating understanding of the diagram of FIG. 3.
Figure 3:
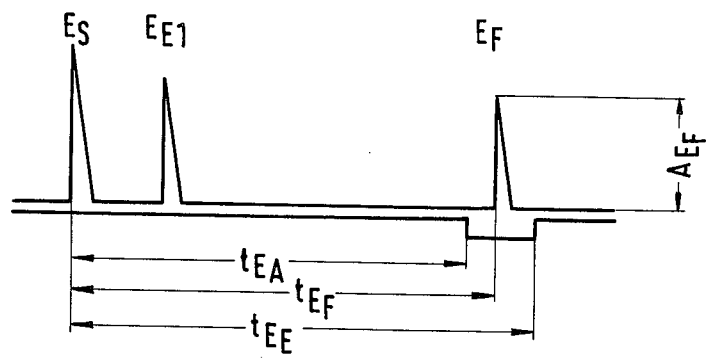
FIG. 3 is a diagram for signals as they occur and are used in accordance with the first phase.

Proceeding now to the detailed description of the drawings, the first and second phases of the operation and procedure in accordance with the preferred embodiment are carried out in a room or location that does not include a production line for the objects to be tested. These objects are, for example, large seam welded pipes with longitudinal welding seam. Accordingly, a dummy 1 is prepared for purposes of simulating the test conditions. However, the dummy 1 is not used directly in the test equipment as installed in the production line for such pipes. Rather, the dummy is used in a separate facility. Moreover, for purposes of these preparation procedures, the dummy needs to represent a portion of such pipe only, namely that portion and zone which participates acoustically in the test procedure.

Reference numerals 4 and 5 refer to two test heads, which include, for example, one or two ultrasonic transducers to be mounted particularly in holders and in particular orientation to external mounting facilities of the holders. The test heads each may include a water column for fluid type coupling of the transducers to the test object.

These test heads are electrically connected to an electronic circuit 8 which generates the necessary pulses and detects echo signals and amplifies them. In addition, the circuit 8 generates gating signals to obtain looking windows for echo signals. The gating signals are applied in the receive circuit to selectively block and to gate open the echo signal path. The gating signals may be derived from a flip-flop which receives on and off or set and reset signals from the outside as will be described. A scope (CRT tube) may be connected to circuit 8 to permit observation of signals and their timing as they occur.

The electronic circuit 8 can be regarded an input-/output device for an acquisition unit 9 being, e.g., a minicomputer, a terminal or the like and receiving the signals generated by and/or received by circuit 8 for purposes of, e.g., metering transit times of echo pulses. Also, the unit 9 provides the command signals for the gating windows to be generated in circuit 8. Such command signals being, e.g., the turn on and off signals for the flip-flop providing the gating signal in circuit 8, whereby particularly the unit 9 meters periods, e.g., in timed relation to the transmitter pulses which periods, in turn, determine phase and length of the looking window; at the end of the respective metered periods appropriate command signals are generated.

Another function of unit 9 is to digitize and to compare amplitudes and to calculate, for example, response thresholds for purposes of rejecting signals arriving from circuit 8. The unit 9 is programmable and through external operation (e.g., keyboard) input unit 9 may acquire additional data such as identification of the particular test head being in any instance coupled to the circuit 8, 9 for the conduction of tests. Also, unit 9 will in some fashion acquire data representing the length of (signal transit time in) the water column or of a Plexiglas-type solid coupler. Also, the distance 7 of a head, such as 5, from the reference or datum plane 6' is inputted as well as the angle and the skip distance. These values become test parameters for locating later a defect found as such on the basis of echo signals.

Adjustment of the head to a particular distance 7, for example, can be detected in that for a given angle 2 of incidence (equivalent to a particularly adjusted transducer orientation in the holder), a jump in the echo must occur when the portion of the bore 6 right at the (convex, outer) surface of the dummy provides the reflection. The same is true for the reverse, wherein for a particular distance 7 the angular position of the transducer holder in head 5 is adjusted.

All relevant data for a particular test head are, by operation of the program in acquisition unit 9 stored in store or memory 10, which as such may be or may become part of the electronics of the test stand. The data includes those mentioned above as well as all relevant transmit times and echo amplitudes and also operational data such as the timing and phasing of the looking windows found suitable during test runs. The system 8, 9, 10 will, therefore, acquire all relevant data for all test heads, and pursuant to test runs on dummy 1.

Before describing test runs, reference is made to FIG. 2. Pursuant to the second phase of the preparatory procedure, dummy 1 is replaced by a test standard 13. That test standard 13 permits coupling of the heads such as 4 and 5 to appropriately selected points. That test standard 13 includes a reflection plane so that a defined US-signal will always be produced. That signal is naturally constant as it depends from the geometrical figuration and the material of that standard only.

Now, particular test runs are conducted with and in the standard 13; this includes the detection of particular echos, their amplitude and their transit time. The circuitry and system 8, 9 and 10 is likewise used for this second set of tests.

Block 11 in FIG. 2 denotes the function of correlating in particular fashion (infra) the test data for the same head and resulting from tests on and with dummy 1, as well as those conducted with standard 13. In reality, one will use the processing facility that was used for data acquisition to execute the relation forming program. The result therefrom is stored in a separate portion of the data store facility being denoted by block 12; that section is also part of the store to be used subsequently for on-production line testing.

It should be noted that the various acquisitions and calculating operations do not have to be carried out through program execution but can be carried out manually. This includes particularly the sequential storing, retrieval and calculations of the various data acquired.

After having described the test room equipment, it will be appreciated that the following preparatory steps and phases are carried out here and prior to installing and completing the production line test stand. As stated, phase 1 includes the use of the dummy 1 in relation to the various test heads and holders. By way of example, head 5 is placed upon dummy 1 (FIG. 3a). The position will be a particular one as far as distance 7 from the reference plane 6' is concerned, being defined by a radial plane (as to the pipe-dummy) through the axis of the bore 6. The angle of incidence for the transducer in test head 5 has been also adjusted. Through keying or the like of the input section that angle is stored as data, so is the distance 7 to thereby identify the particular region to be investigated as to flaws, such flaw being simulated by the bore 6.

In a first test run, a transmitter pulse is generated resulting in an immediate echo pulse Es, a reflection $E_{E1}$ at the head-dummy interface, and an echo $E_F$ at the test defect. The transit time $T_{EF}$ is ascertained in unit 9 through clock pulse counting and the resulting value is stored as data in store or memory 10. The electronic circuit 8 provides also looking windows for purposes of noise suppression, enabling the receiving of ultrasonic pulses for a short period of time only in which defect echos must occur in order to be recognized as such. This looking window is represented by a gating signal which can be taken from a suitable test point in electronic circuit 8 to be displayed by the scope. The window-gating signal will begin a particular delay period $t_{EA}$ following the transmitter echo Es, and will end at a particular delay $t_{EE}$ also measured from the instant of the signal Es.

These delay periods are, e.g., keyed-in by the operator as commands to be used in relation to the timing of EF as observed by him. As stated, these periods $t_{FA}$ and $t_{EE}$ will then be metered by counting internal clock pulses until the keyed-in values have been reached, and trigger signals are then transmitted to electronic circuit 8 to turn the gating window generating flip-flop on and off, respectively. Having found by trial and error a suitable flaw echo acquisition window, the final values for $t_{EA}$, $t_{EF}$ and $t_{EE}$ are stored in memory 10 under the appropriate identification of the test head, angles of incidence, distance, etc. In addition, the period Es–$E_{E1}$ may be metered to represent the transit time of echos through the water column or the specific coupler medium used in the particular test heads. Another value being acquired now and stored in memory is the amplitude $A_{EF}$ of the "defect" echo $E_F$.

As far as the head 5 is concerned, this completes the first phase. However, similar procedures are carried out for other test heads in other positions such as the symmetrically positioned head 4, but also for heads having different distances, angles of incidence and skip distances for inspecting different zones in the welding seam as to longitudinal flaws.

Figure 4A:
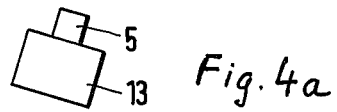
FIG. 4a is a sketch for facilitating understanding of the diagram of FIG. 4.
Figure 4:
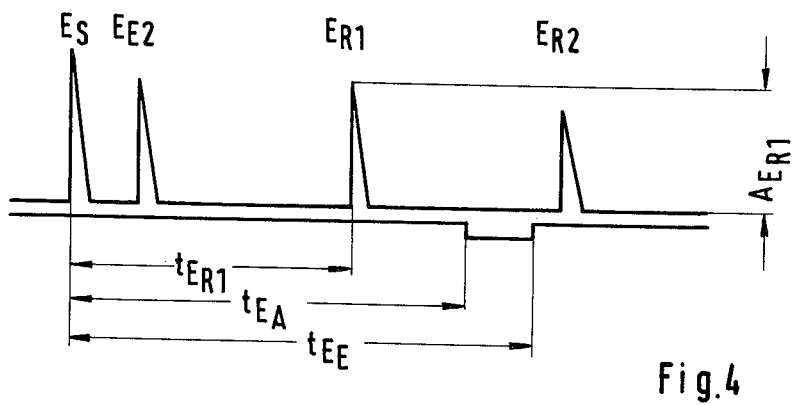
FIG. 4 is a diagram for signals as they occur and are used in accordance with the second and a third phase.

The second phase maintains the internal orientation of the test head (or heads), i.e., its transducer adjustment, but the dummy 1 is removed from under the test head, and replaced by the standard 13 (FIG. 4a). Now, the electronics is run to generate signals as shown in FIG. 4. The internal adjustment of head 5 remains fixed, and the standard 13 is placed so that the resulting position of the head 5 on the standard represents uniquely the ultimate test position of the test head, but now being defined with respect to the standard.

A test run now results in a transmitter echo pulse Es; an entrance echo $E_{E2}$ from reflection at the interface between head and standard; a first rear wall echo $E_{R1}$ and a second rear wall echo $E_{R2}$, the latter resulting when the first rear wall echo is partially reflected again at the interface. As stated, the timing of these echos is indeed representative of the test position of head 5. This is particularly true also with regard to the adjustment of the transducer or transducers in the holder of head 5.

As far as this second phase is concerned, of particular interest are, the amplitude of that first rear wall echo AERI; and the transit time of $E_{R1}$ ($t_{ER}$). These values are acquired and also stored. Then or later, the processor 9 will generate the following three values: AERI-AEF in representation of the test head sensitivity and the two periods $t_{EA}-t_{ER1}$, and $t_{EE}-t_{ER1}$. Since the test head distance 7, the relevant skip distance, the angle of incidence of the beam, the desired or needed threshold and the level and amplitude range of flaw echo signals, are given otherwise, the various reference signals can now be determined and calculated, they are stored in the memory 12 and become a permanent part of the test equipment and the reference file.

The test heads are now installed in the test equipment of the production line. The particular orientation of the transducers in the test heads is, of course, maintained, and the disposition and distance of the heads are, so to speak, transferred to the on-line test stand by means of the standard 13 to fix the disposition and spacing of the heads in relation to the true test objects.

It should be mentioned that the preparatory procedure was and is being described with reference to ultrasonic inspection for purposes of detecting longitudinally extending flaws. Transverse flaw detecting and edge zone testing equipments are initialized in the same or analogous manner using the dummy and a standard. Now, as to each head such as 5 and having been mounted in the on-line stand, the standard 13 is again applied. The store 12 is now used in the test acquisition processor, possibly also part or all of electronics 8 and unit 9, though test room equipment and on-line test electronics may be different instruments and EDP equipment. Also, neither scope nor manual data inputs are needed if this third phase and test program is run by computer facilities.

On the basis of the previously determined and stored rear wall echo ERI and its transit time $t_{ER1}$, a looking window for a rear wall echo from standard 13 is now calculated and used in an on-site test run, solely for purposes of acquiring a new rear wall echo pulse ERI*, its transit time $t_{E^*R1}$, and its amplitude $A_{E^*R1}$. Any subjective errors in the installation and adjustment are automatically taken care of by the new acquisition of these values.

Using these values, as well as the previously acquired data AERI-AEF; $t_{EA}-t_{ER1}$, $t_{EE}-t_{ER1}$, the relevant data for the test operations are calculated. Particularly, the differential AERI-AEF and the newly acquired amplitude $A_{E^*R1}$ are used to calculate the expected test levels on the basis of the known relation between the test response threshold and the previously acquired value AEF, now being updated by operation of this transposition. Analogously, the new transit time $t_{E^*R1}$ is used to calculate new values for beginning and end of the operational looking window on the basis of the stored values $t_{EA}-t_{ER1}$ and $t_{EE}-t_{ER1}$. These newly calculated values are then metered following each transmitter pulse to open and reclose the looking window in the echo signal processing circuit, to limit its response to echo pulses as they may occur during the respective gating and window period.

It can thus be seen that the standard 13, as well as the stored reference data are used for on-line initialization of the equipment. It can also be seen that the original dummy is no longer needed and for each new on-line initialization, one can use the standard 13 and the reference data once acquired.

In furtherance of the invention, the method can be expanded to be used to offset, e.g., drift problems or the like. For this, one will use a dynamic supervision of the test stand equipment. It should be noted that in view of the large number of tests and test functions involved, it is not practical to halt the line and to test the test equipment with known methods. Rather, it is proposed to use a particular test object, e.g., a test pipe which, e.g., was found defective and is now being provided with particular flaws, such as a (radial) bore through the seam. That test pipe is occasionally passed through and tested, and the "defect" detected is now used to determine whether or not initialization needs correction.

The invention is not limited to the embodiments described above but all changes and modifications thereof not constituting departures from the spirit and scope of the invention are intended to be included.

We claim:

1. Method of initializing and preparing an ultrasonic test stand in a production line for on-line testing of production objects in and passing through the line, comprising the steps of:

provarding a dummy, representing a zone of a production object to be traversed by ultrasonic radiation dummy testing;

orienting and positioning an individual test head with reference to said dummy in particular relation to the zone;

conducting first ultrasonic tests by means of the test heads as oriented and positioned under utilization of test circuitry, the tests including (i) generating and launching a test pulse into the dummy, (ii) detecting a particular return echo, (iii) determining an amplitude of the return echo, and (iv) adjusting the timing of a particular gating period on the basis of the detected occurrence of the said return echo;

replacing the dummy by a standard for each test head;

conducting second ultrasonic tests by means of the test heads and the standard and under utilization of the same test circuitry as in the first tests, the second tests including (i) generating and launching a test pulse into the standard; (ii) detecting a particular return echo; (iii) determining an amplitude of the latter return echo; and (iv) determining the transit time of the latter return echo;

arithmetically relating and referencing (i) the amplitudes as acquired pursuant to said first and second tests as conducted and separately for each test head, to obtain amplitude calibration signals; and (ii) arithmetically relating the adjusted timing of the gating period as per the first tests and the transit times of the return echos as per the second tests to obtain timing calibration signals, also separately for each test head;

storing the amplitude and timing calibration signals;

placing the test heads in positions in said test stand being the same or corresponding positions the test heads had in relation to said dummy during the first mentioned conducting test;

repeating the second ultrasonic tests conducting step with the test head in test stand position but with said standard in position as in said second conducting step and under utilization of a different test circuit to obtain again an amplitude and a transit time for a return echo; and using the amplitude and transit time data as acquired pursuant to the last mentioned, repeated conducting step and the stored amplitude and timing calibration signals, for adjusting the said test circuit to obtain therein a particular gating period and amplitude response for the subsequent on line testing.

2. Method as in claim 1, wherein the relating step (i) includes relating the amplitude of an echo from a particularly flaw in the dummy and the amplitude of an echo by a boundary of the standard.

3. Method as in claim 1, wherein the relating step (ii) includes the formation of differences between the transit time of an echo by a boundary of the standard, and at least one relevant time and phase of a looking window in which a dummy defect signal occurs, in relation to a transmitter signal as launched pursuant to the second tests.

4. Method as in claim 1, and including subsequent recalibration by means of a test object with predetermined defects during and interspaced with regular production testing.

* * * * *